(12) United States Patent
Chen et al.

(10) Patent No.: US 9,023,623 B2
(45) Date of Patent: May 5, 2015

(54) METHOD FOR PREPARING OF ALLICIN INJECTION AND LOW-TEMPERATURE CONTINUOUS STIRRING ULTRAFILTRATION DEVICE THEREOF

(71) Applicant: Xinjiang Ailexin Pharmaceutical Co., Ltd., Urumqi (CN)

(72) Inventors: Jian Chen, Urumqi (CN); Xinxia Li, Urumqi (CN)

(73) Assignee: Xinjiang Ailexin Pharmaceutical Co., Ltd., Xinjiang (CN)

( * ) Notice: Subject to any disclaimer, the term of this patent is extended or adjusted under 35 U.S.C. 154(b) by 10 days.

(21) Appl. No.: 13/725,898

(22) Filed: Dec. 21, 2012

(65) Prior Publication Data

US 2013/0154138 A1    Jun. 20, 2013

Related U.S. Application Data

(63) Continuation of application No. PCT/CN2011/000959, filed on Jun. 8, 2011.

(30) Foreign Application Priority Data

Jun. 22, 2010  (CN) .......................... 2010 1 0205840

(51) Int. Cl.
| | |
|---|---|
| *C12P 13/12* | (2006.01) |
| *A61J 3/00* | (2006.01) |
| *A61K 9/00* | (2006.01) |
| *A61K 9/08* | (2006.01) |
| *A61K 31/255* | (2006.01) |
| *C12P 11/00* | (2006.01) |

(52) U.S. Cl.
CPC ................. *A61J 3/00* (2013.01); *A61K 9/0019* (2013.01); *A61K 9/08* (2013.01); *A61K 31/255* (2013.01); *C12P 11/00* (2013.01); *C12Y 404/01004* (2013.01)

(58) Field of Classification Search
None
See application file for complete search history.

(56) References Cited

U.S. PATENT DOCUMENTS

| 7,179,632 B2 * | 2/2007 | Williams et al. .............. 435/232 |
| 7,901,717 B1 * | 3/2011 | Falkenberg et al. .......... 424/754 |
| 2004/0247711 A1 * | 12/2004 | Williams et al. .............. 424/754 |
| 2005/0031715 A1 * | 2/2005 | Kyung .......................... 424/754 |
| 2005/0249952 A1 * | 11/2005 | Vasishtha et al. ......... 428/402.24 |
| 2011/0027341 A1 * | 2/2011 | Mirelman et al. ............ 424/430 |

FOREIGN PATENT DOCUMENTS

| CN | 2497861 Y | 7/2002 |
| CN | 1465283 A | 1/2004 |
| CN | ZL 00101244.4 | 7/2004 |
| CN | ZL 03100420.2 | 5/2005 |
| CN | ZL 03100419.9 | 10/2005 |
| CN | 1830423 A | 9/2006 |
| CN | 102058527 A | 5/2011 |
| JP | 58-067626 | 4/1983 |
| WO | WO 97/39115 | 10/1997 |
| WO | WO 03/004668 A1 | 1/2003 |

OTHER PUBLICATIONS

Butler et al., Abstract (1994).*
Canizares et al., Biotechnol. Prog., 20:32-37 (2004).*
Jacob, Nat. Prod. Rep., 23, 851-863 (2006).*
International Search Report of International Application No. PCT/CN2011/000959, dated Sep. 8, 2011.

* cited by examiner

*Primary Examiner* — Blaine Lankford
*Assistant Examiner* — Thomas J Visone
(74) *Attorney, Agent, or Firm* — J.C. Patents

(57) ABSTRACT

The present invention provides a preparing method of an allicin injection and the low temperature continuous stirring ultrafiltration device thereof. Said preparing method consists of the following steps: extracting allicin; diluting the allicin with solvent precooled to 1-4 in a clean environment, adding nitrogen gas or argon gas, and then encapsulating the solution to obtain allicin injection with different specifications.

7 Claims, 2 Drawing Sheets

METHOD FOR PREPARING OF ALLICIN INJECTION AND LOW-TEMPERATURE CONTINUOUS STIRRING ULTRAFILTRATION DEVICE THEREOF

CROSS-REFERENCE TO RELATED APPLICATIONS

This application is a continuation of International Application No. PCT/CN2011/000959, filed on Jun. 8, 2011, which claims the priority benefit of Chinese Patent Application No. 201010205840.3, filed on Jun. 22, 2010. The contents of the above identified applications are incorporated herein by reference in their entireties.

FIELD OF THE TECHNOLOGY

The present invention relates to the pharmaceutical field, specifically, relates to a method for preparing an anti-tumor and anti-infection allicin injection, and a low-temperature continuous stirring ultrafiltration device thereof.

BACKGROUND

Garlic (*Alliium sativun* L.) and its related preparations are included in the United States Pharmacopoeia and European Pharmacopoeia. Alliin and allicin are confirmed as the major active ingredients. But the content of alliin or allicin in garlic preparations in the market at home and abroad is very low. Research and development of new garlic preparations with safety, effectiveness and controllable quality has attracted more and more attention among researchers around the world.

1. Alliin

Chemical name: S-Allyl-L-cysteine sulfoxide

Melt point: 163-165° C. (decompose and carbonize)

Specific rotation: $[\alpha]_D = +60°$

White crystalline powder, and almost odorless.

Structure:

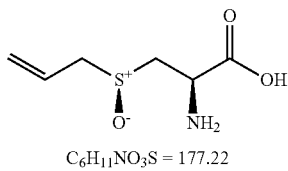

$C_6H_{11}NO_3S = 177.22$

Molecular Weight: 177.22.

Patents cited: In a method of extracting alliin from fresh garlic (ZL 001012444) and a producing process for extracting alliin from fresh garlic (ZL 03100420.2), garlic which is in compliance with the garlic monograph in Pharmacopoeia is peeled and washed with pure water, then subjected to inactivation of alliinase under microwave radiation for 5-10 minutes or by boiling with boiling water for 5-10 minutes. The inactivated garlic is pulped, extracted with pure water or 5-70% alcohol, concentrated, filtered, absorbed with ion exchange column chromatography, eluted with ammonia, concentrated, and dried by spray-drying, and then the alliin as pharmaceutical raw material is obtained by recrystallization. Alliin content: ≥90%, according to HPLC analysis.

2. Alliinase (EC 4.4.1.4)

Synonym: Alliin lyase, S-allyl-L-cysteine sulfoxide lyase

Alliinase is a glycoprotein dipolymer, where the molecular weight of the two subunits is 51.5 KDa. It is a yellowish crystal, odorless, and the isoelectric point is 4.9.

Patents cited: In a producing process for extracting alliinase from fresh garlic (ZL 03100419.9), garlic which is in compliance with the garlic monograph in Pharmacopoeia is peeled and washed with pure water. The peeled garlic is pulped with colloid mill and alliinase is extracted therefrom with a protective buffer solution. After precipitation of alliinase with $(NH_4)_2SO_4$ or PEG-4000~8000, the precipitation is collected with a continuous low-temperature tube centrifuge. Then the precipitation is again dissolved in the protective buffer solution. After removal of the macromolecule and micromolecule substances with two sets of ultrafiltration devices, respectively, the buffer solution is subjected to lyophillization to obtain alliinase as pharmacal raw material. The enzyme activity of alliinase is ≥1000 IU/g determined by HPLC with alliin as substrate.

3. Allicin

Chemical name: thio-2-propene-1-sulfinic acid S-allyl ester

Density: $1.112 \text{ g/cm}^3$

Melt point: 25° C. (decompose)

Molecular weight: 162.3

Allicin is faint yellow volatile viscous liquid at room temperature, slightly soluble in water, and with strong odour. Allicin decomposes and deteriorates within a few hours when exposed to air.

One Allicin molecule is formed by catalytic decomposition of two alliin molecules by alliinase, i.e., 354.4 g alliin $(2[C_6H_{11}NO_3S]=2\times177.2=354)$ can form 162.3 g Allicin $([C_6H_{10}OS_2]=162)$. The yield is about 90%. The production can be calculated as follows:

$$\text{Production of allicin} = \text{mass of alliin} \times C \times (162.2/354.4) \times 0.9$$

where C represents purity of alliin added, and 0.9 represents the reaction coefficient.

Reaction formula is as follows:

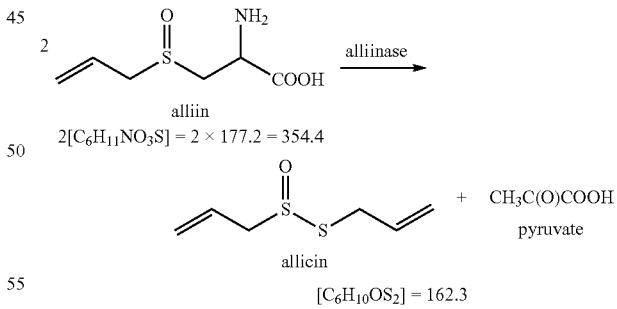

SUMMARY

In order to solve the problem mentioned above, one object of the present invention is to provide a process for preparing an anti-tumor and anti-infection allicin injection, which has the advantages of reasonable formulation, simplicity in preparation, high purity and stable properties.

In order to achieve the object mentioned above, the present invention adopts the following technical solution:

A method for preparing an anti-tumor and anti-infection allicin injection comprises the following two steps:

first step, extracting allicin, which comprises the following steps:

(1) adding alliinase and deoxygenated pure water to a container filled with argon or high purity nitrogen with a water-to-alliinase ratio of 1000~2000 ml:35.4 g, stirring thoroughly to dissolve the alliinase completely, and adjusting the temperature of water bath to 25-35 and adjusting pH to 6.5-8.5, to obtain an alliinase solution, where the water-to-alliinase ratio can be increased or decreased according to the yield and concentration as desired;

(2) preparing an alliin solution in an alliin-to-water ratio of 35.4 g:500~1000 ml, and slowly dropping the alliin solution into the container containing the alliinase solution, stirring thoroughly and filling continuously the container with high purity nitrogen or argon to fully fill the container with the high purity nitrogen or argon, where the ratio of alliin to alliinase is 1 mg:1~2 IU;

(3) after completion of the dropping addition of the alliin solution, continuously stirring and reacting for 20 to 40 minutes in total to obtain an enzymolysis reaction solution containing allicin and other components, and then immediately replacing the warm bath water with ice water to low down the temperature of the water bath (containing excess ices) to 0, and finally, using an ultrafiltration membrane of 1000~5000 D to remove the alliinase and obtain an aqueous solution of allicin;

second step, diluting the allicin extracted in above first step with a solvent precooled to a temperature of 0-4° C. under a clean bio-safety cabinet (sterile) environment, to obtain allicin solution;

encapsulating the above allicin solution into different specification ampoules filled with nitrogen or argon as required, to obtain allicin injection, which is used to treat septicemia or tumors by intravenously guttae.

The concentration of the allicin produced according to the present invention is 1.0 mg/ml, 2.0 mg/ml, 2.5 mg/ml and 5.0 mg/ml. The specification of allicin injection is 1 ml/Amp, 2 ml/Amp, 5 ml/Amp and 10 ml/Amp. The injection is packed in brown cases and stored at 0~−20° C., with the shelf life of 6-12 months.

The solvent can be deoxygenated pure water, or deoxygenated pure water containing cryoprotectant ethanol, or deoxygenated pure water containing cryoprotectant propylene glycol.

The purity of alliin can be no less than 90%.

The enzyme activity of alliinase can be no less than 1000 IU/g.

The stirring speed can be 60~120 rpm.

The deoxygenated pure water can be is such water that is freshly boiled and naturally cooled and then filled with high purity nitrogen or argon at the bottom at 1 h/10 L, to remove the dissolved oxygen existing in the water.

Another object of the present invention is to provide a low-temperature continuous stirring ultrafiltration device for production of an anti-tumor and anti-infection allicin injection. The device comprises a wide neck container with a heat preservation case and a refrigeration platform on which the wide neck container is placed. An ultrafiltration membrane separates the container into an upper compartment and a lower compartment along the cross section of the container, the upper compartment is equipped with a stirring device and a gas inlet through which the high purity nitrogen or argon enters the container; and the lower compartment is equipped with a liquid suction device for draining the allicin solution after removal of alliinase.

Pharmacodynamic Test Data

Allicin injection prepared according to the method of the present invention was used to conduct clinic pharmacodynamic test. Allicin injection with specification of 5.0 mg/ml was used to conduct the anti-tumor test in Shanghai Medicilon Inc. and the anti-pathogenic microorganism test in the First Teaching Hospital of Nanjing Medical University. The results showed that allicin injection is effective on a variety of pathogenic microorganism and tumors. Test specimen was provided for clinical trial and new drug registration. The specific experimental data are as follows:

1. Anti-Tumor Test Results from Shanghai Medicilon Inc.

The results in table 1 showed that the Inhibitory Concentration 50 (IC50) of Taxol on various kinds of cells is about 10 nM or below 10 nM, indicating that, according to the guiding principle of anti-tumor pharmacodynamics (the IC50 of the pure extract from a plant should be <10 µg/ml and the IC50 of the crude extract from a plant should be 620 µg/ml), allicin injection has obviously in vitro antipersonnel effect on these cell strains. The IC50 of allicin to 13 of the cell strains is substantially bellow 10 µg/ml, indicating that, allicin has in vitro antipersonnel effect on the thirteen cell strains.

2. Anti-Pathogenic Microorganism Test Results from the First Teaching Hospital of Nanjing Medical University The results from series test showed that allicin has obviously bactericidal activity to Methicillin Resistant *Staphylococcus Aureus* (MRSA), *Acinetobacter, Escherichia coli, Helicobacter pylori, Candida albicans* and so on. Especially, MRSA and *Helicobacter pylori* is more sensitive to allicin, and has MIC of 10~30 mg/L. In addition, *Candida albicans* is also sensitive to allicin. Allicin is a hopeful candidature drug instead of vancocin for treatment of infection disease caused by MRSA. Allicin could be used for treatment of gastritis and gastrelcoma caused by *Helicobacter pylori*. Allicin also could be used as therapeutic drugs for yeast-like fungal infection (for oral use or external use).

TABLE 1

| | | The values of IC50 Operator: Ding Haili, Xia Chunxia Date: 2009.11.11 | | | | | |
|---|---|---|---|---|---|---|---|
| | cells/ | $IC_{50}$ of Allicin (µg/ml) | | | $IC_{50}$ of Taxol (nM) | | |
| Cell line | well | 1 | 2 | 3 | 1 | 2 | 3 |
| BGC823, gastric carcinoma cell line | 5000 | 6.318 ± 1.09 | 5.679 ± 1.07 | 6.192 ± 1.07 | 9.182 ± 1.05 | 9.071 ± 1.05 | 9.302 ± 1.05 |
| HT-29, moderately differentiated colon carcinoma cell of human | 5000 | 6.282 ± 1.07 | 7.733 ± 1.07 | 6.980 ± 1.08 | 4.72 ± 1.11 | 8.365 ± 1.20 | 7.155 ± 1.10 |
| Hep3B, SMMC-7721 | 5000 | 4.917 ± 1.05 | 4.980 ± 1.04 | 4.564 ± 1.03 | 6.793 ± 1.06 | 6.211 ± 1.07 | 6.897 ± 1.04 |
| MCF-7, breast carcinoma cell line | 5000 | 5.853 ± 1.11 | 8.075 ± 1.10 | 10.9 ± 1.117 | 4.259 ± 1.06 | 3.308 ± 1.05 | 8.331 ± 1.16 |

TABLE 1-continued

The values of IC50
Operator: Ding Haili, Xia Chunxia    Date: 2009.11.11

| Cell line | cells/well | $IC_{50}$ of Allicin (µg/ml) | | | $IC_{50}$ of Taxol (nM) | | |
|---|---|---|---|---|---|---|---|
| | | 1 | 2 | 3 | 1 | 2 | 3 |
| MDA-MB-435S, breast carcinoma high transitional cell | 5000 | 10.98 ± 1.04 | 11.34 ± 1.03 | 10.90 ± 1.05 | 0.226 ± 0.9 | 0.215 ± 0.9 | 0.212 ± 0.9 |
| PC-3, prostate cancer cell line | 5000 | 6.583 ± 1.07 | 6.908 ± 1.06 | 7.868 ± 1.08 | 0.220 ± 0.6 | 0.443 ± 0.87 | 1.007 ± 1.00 |
| K562, chronic myelogenous leukemia | 5000 | 6.302 ± 1.06 | ~5.884 | 5.817 ± 1.05 | 1.067 ± 1.01 | 0.6040.89 | 0.878 ± 0.98 |
| Jurkat E6-1, acute T cell leukemia | 5000 | 1.132 ± 1.28 | 1.401 ± 1.27 | 1.231 ± 1.14 | ~1.607 | 1.701 ± 1.15 | 1.406 ± 1.04 |
| L1210, mice leukemic cell | 2000 | 2.266 ± 1.20 | 2.090 ± 1.36 | 1.542 ± 1.19 | 25.76 ± 1.14 | 22.79 ± 1.16 | 25.80 ± 1.16 |
| ZR-75-1, breast carcinoma cell line | 4000 | 5.466 ± 1.12 | 3.019 ± 1.30 | 4.759 ± 1.13 | 27.35 ± 1.39 | 21.56 ± 1.40 | 12.22 ± 1.19 |
| HCT116, human large intestine cancer cell line | 3000 | 3.721 ± 1.10 | 4.258 ± 1.15 | 3.542 ± 1.09 | 5.756 ± 1.04 | 5.526 ± 1.04 | 5.956 ± 1.04 |
| PANC-1, pancreatic cancer cell line | 5000 | 5.972 ± 1.02 | 5.941 ± 1.05 | ~6.204 | 8.043 ± 1.09 | 7.430 ± 1.11 | 6.420 ± 1.09 |
| A549, lung cancer cell line | 5000 | 6.321 ± 1.10 | 6.327 ± 1.08 | 8.032 ± 1.04 | 1.129 ± 1.02 | 1.388 ± 1.04 | 0.659 ± 0.9 |

Beneficial Results

The present invention provides a method production of allicin by catalytic decomposition of alliin with alliinase under conditions of inert gas protection and enclosed air-isolation environment, which has never been reported. The technology of ultrafiltration under icewater bath for removing alliinase is used for the first time. Decomposition of allicin has decreased under these conditions. The yield of allicin is no less than 90%. All these procedures are operated in bio-safety sterile cabinet (the cleanliness rank is 100).

After determining the content of allicin with HPLC, allicin injection is prepared in ampoule filled with argon or nitrogen and sealed. Specifications are 1.0~10.0 mg/ml×1.0 ml; 1.0~10.0 mg/ml×2.0 ml; 1.0~10.0 mg/ml×5.0 ml; 1.0~10.0 mg/ml×10.0 ml. Preserved at 0~4° C. shielded from light for 6 months, no obviously alteration of content was observed. No obviously alteration of content was observed after storage at −10° C. shielded from light for 24 months with addition of 20% ethanol and/or propylene glycol cryoprotectant.

The present invention involves enzyme catalysis dynamics and ultrafiltration technologies for new drug development. Alliin and alliinase extracting from fresh garlic are used as raw materials. With special devices in bio-safety cabinet under protection of argon or nitrogen (inert gas), synthesis of allicin is operated by catalytic decomposition of alliin with alliinase. The reaction solution is stirred at under low temperature and filtered with ultrafiltration membrane to remove alliinase. The content of allicin is determined by HPLC, and the allicin is diluted quantitatively with particular mediums, for example, deoxygenated water, ethanol or propylene glycol and so on, to obtain an allicin solution. the allicin solution is introduced into ampoules filled with nitrogen, and then the ampoules are sealed to obtain the allicin injection. It has been proved that the allicin injection is effective against many pathogenic organisms and tumor cell. The allicin injection can be provided as the test specimen for clinical trial and for new drug registration.

BRIEF DESCRIPTION OF THE DRAWINGS

The figures are provided for to further comprehension of this invention and construct a part of the description. They are used to explain the present invention in combination with embodiments, but not intended to limit the present invention.

The reference signs in figures of this invention is illustrated in the following:

A—three-necked bottle, P—pump for sampling, M—enclosed type blender, I—water bath, G—gas inlet, R—Bio-safety Cabinet (cleanliness of 100, sterile), C—heat preservation case, H—ultrafiltration membrane, S—blender, and T—refrigeration platform.

DETAILED DESCRIPTION

The preferred embodiments of this invention will be illustrated with reference to the figures in the following. It should be understood that the preferred embodiments described here are only intended to illustrate and interpret, but not to limit this invention.

Embodiment 1

Figure 1:
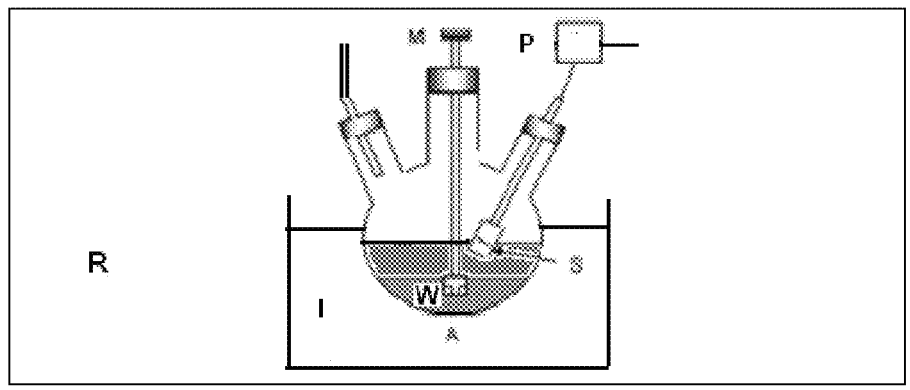
FIG. 1 is a schematic diagram of the device for synthesis of allicin by alliinase catalyzing alliin according to the invention.
Figure 2:
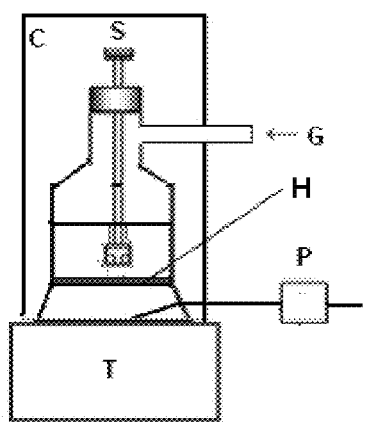
FIG. 2 is a schematic diagram of low-temperature continuous stirring ultrafiltration device according to the invention.
Figure 3:
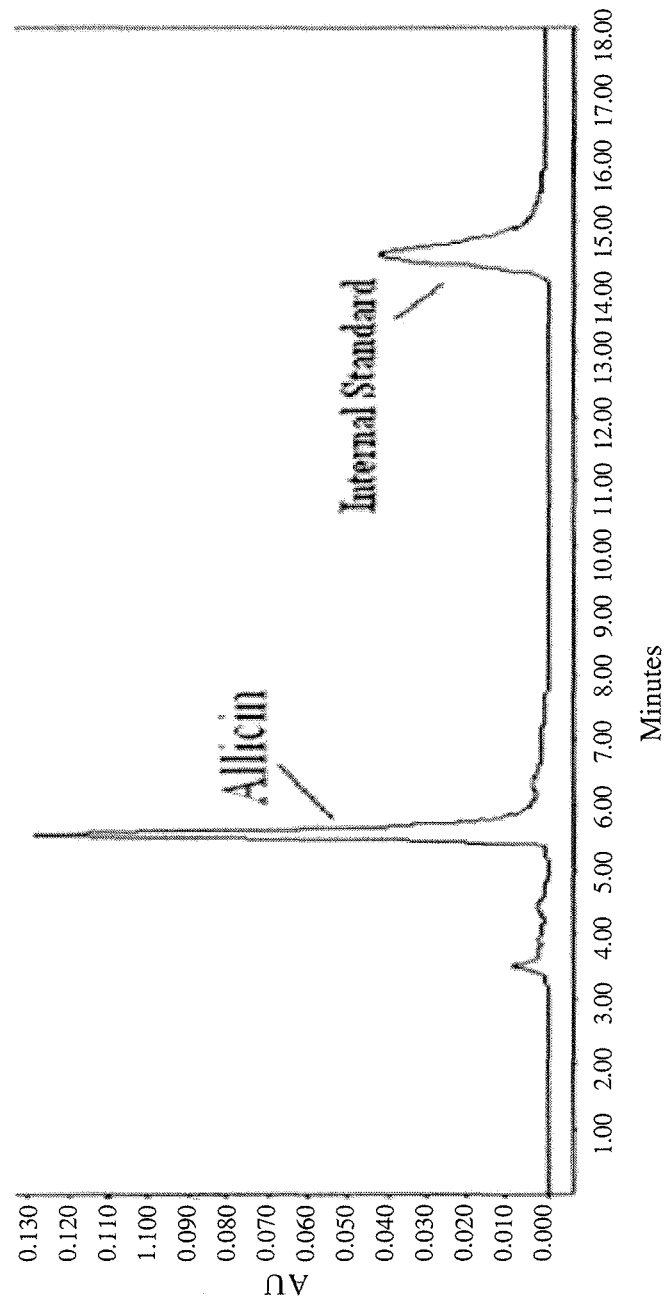
FIG. 3 is a HPLC chromatogram of allicin injection with the concentration of 5.0 mg/ml according to the invention.

FIGS. 1-3 are schematic diagrams of embodiments according to this invention. The preparation method of allicin injection is as follows:

(1) Add approximately 1000~2000 ml of deoxygenated pure water into a 5000 ml three-necked bottle A, add 35.4 g of alliinase, and stirr thoroughly (M, 60 rpm) to completely dissolve the alliinase to obtain an alliinase solution Adjust the temperature of water bath 1 to 25-35° C., check and confirm that the solution has a pH in the pH range of 6.5-8.5;

(2) Add about 500~1000 ml of deoxygenated pure water into an enclosed type separatory funnel, add 35.4 g alliin, and then gently shake the enclosed type separatory funnel to dissolve the alliin, and fill the three-necked bottle G with high purity nitrogen or argon simultaneously;

(3) While stirring (M, 60 rpm), dropwise add the alliin solution into the three-necked bottle A at speed of 50 ml/min through opening B of the enclosed type separatory funnel, after completion of the dropwise addition of the alliin solution, keep stirring the mixed solution for 10 minutes, and the total reaction is about 30 min to obtain an enzymolysis reaction solution containing allicin and so on, and then replace the warm bath water with ice water immediately to lower down the temperature of the water bath to 0° C. The device is shown in FIG. 1.

The enzymolysis reaction conditions are: temperature of the reactor is 25-35° C., the pH of the aqueous solution is 6.5-8.5 and the reaction time is about 30 min. The key for successful preparation of the allicin is to keep the allicin stable chemically. The present invention uses inert gas protection to isolate from air and the temperature is lowered to a low temperature (0° C.) immediately at the end of the reaction (about 30 min from the beginning of dropwise adding alliin).

A low temperature stirring ultrafiltration device (FIG. 2) is installed in a bio-safety cabinet. The reaction solution W was taked out and transferred to a pressure flask with a ultrafiltration device by a pump. The refrigeration platform T was adjusted to a temperature of −2° C. and sheathed with a heat preservation case C. The blender S was started and simultaneously a cylinder of high purity and high pressure nitrogen was connected to the gas inlet G. Alliinase and other macromolecules were removed from the solution using ultrafiltration membrane H of 1000~5000 D at a predetermined pressure, to gain about 1500~3000 ml of allicin solution A with alliinase being removed.

In a clean bio-safety cabinet, appropriate amount of allicin solution A was taked to determine the allicin content by High Performance Liquid Chromatography (HPLC). Then the solution A was diluted with precooled deoxygenated pure water (or deoxygenated pure water with addition of ethanol or propylene glycol cryoprotectant) to gain about 1500 ml of 10.0 mg/ml or about 3000 ml of 5.0 mg/ml allicin solution. The allicin content was again determined by HPLC, which conform to 98%-102% of the labelled amount.

Embodiment 2

The preparation method of allicin injection was as follows:

(1) Add 35.4 g alliinase with the enzyme activity of not less than 1000 IU/g and 1000 ml deoxygenated pure water to a container, stiffing thoroughly (M, 60 rpm) to completely dissolve the alliinase, adjusting the temperature of water bath to 25° C., and controlling the pH at 6.5, to obtain an alliinase solution, wherein the pure water was such water that was freshly boiled and naturally cooled, and then high purity nitrogen or argon was introduced at a speed of 10 L/h into the water from bottom to remove dissolved oxygen therein;

(2) Prepare an alliin solution, where the ratio of alliin to deoxygenated pure water was 35.4 g: 500 ml, dropwise add the alliin solution to the above container slowly, stirring thoroughly at a stirring speed of 60 rpm and continuously filling high purity nitrogen or argon so that the container was fully filled with the high purity nitrogen or argon, where the ratio of alliin:alliinase is 1 mg:1 IU, and the purity of alliin is higher than 90%;

(3) After completion of dropwise addition of the alliin solution, keep stirring the mixed solution to conduct reaction for about 20 min in total, to obtain an enzymolysis reaction solution containing allicin and so on, and then immediately replace the warm bath water with ice water to lower down the temperature of water bath to 0° C., and finally, an ultrafiltration membrane of 1000 D was used to remove the alliinase and obtain an aqueous solution of allicin.

In the second step, the allicin formed in step 1 was diluted with precooled solvent (0° C.) in clean environment to obtain an allicin solution. The solvent was deoxygenated pure water, or deoxygenated pure water containing ethanol cryoprotectant, or deoxygenated pure water containing propylene glycol cryoprotectant.

The allicin solution above was encapsulated into different specification ampoules filled with nitrogen or argon as required and sealed. The therapeutics use of this allicin injection is for septicemia or tumors by intravenously guttae.

The concentration of allicin produced above is 1.0 mg/ml. The specification of allicin injection is 1 ml/Amp. The injection was packed with brown case and stored in 0~−20° C. The keeping time is 6-12 months.

A low-temperature continuous stirring ultrafiltration device for production of allicin injection comprises a wide neck container with a heat preservation case and a refrigeration platform. The wide neck container is placed on the plateform. An ultrafiltration membrane separates the container into two parts along the cross section of the container: the upper compartment, which is equipped with a stirring apparatus and a gas inlet through which high purity nitrogen or argon enters; and the lower compartment, which is equipped with a liquid suction device for draining the allicin solution after removal of alliinase.

Embodiment 3

(1) Add 35.4 g alliinase with the enzyme activity of not less than 1000 IU/g and 2000 ml deoxygenated pure water to a container, stirring thoroughly at a stirring speed of 120 rpm to completely dissolve the alliinase, adjusting the temperature of water bath to 35° C., and controlling the pH at 8.5, to obtain an alliinase solution, wherein the pure water was such water that was freshly boiled and naturally cooled down, and then high purity nitrogen or argon was introduced at a speed of 10 L/h into the water from bottom to remove dissolved oxygen therein;

(2) Prepare an alliin solution, where the ratio of alliin to deoxygenated pure water was 35.4 g: 1000 ml, dropwise add the alliin solution to the above container slowly, stiffing thoroughly at a stiffing speed of 60 rpm and continuously filling high purity nitrogen or argon so that the container was fully filled with the high purity nitrogen or argon, where the ratio of alliin:alliinase is 1 mg:2 IU, and the purity of alliin is higher than 90%;

(3) After completion of dropwise addition of the alliin solution, keep stirring the mixed solution to conduct reaction for about 40 min in total, to obtain an enzymolysis reaction solution containing allicin and so on, and then immediately replace the warm bath water with ice water to lower down the temperature of water bath to 4° C., and finally, an ultrafiltration membrane of 5000 D was used to remove the alliinase and obtain an aqueous solution of allicin.

In the second step, the allicin formed in step 1 was diluted with precooled solvent (4° C.) in clean environment to obtain an allicin solution. The solvent was deoxygenated pure water, or deoxygenated pure water containing ethanol cryoprotectant, or deoxygenated pure water containing propylene glycol cryoprotectant.

The allicin solution above was encapsulated into different specification ampoules filled with nitrogen or argon as required and sealed. The therapeutics use of this allicin injection is for septicemia or tumors by intravenously guttae.

The concentration of allicin produced above is 2.0 mg/ml. The specification of allicin injection is 2 ml/Amp. The injection was packed with brown case and stored in 0~−20° C. The keeping time is 6-12 months.

A low temperature continuous stirring ultrafiltration device for production of allicin injection comprises a wide neck container with a heat preservation case and a refrigeration platform. The wide neck container is placed on the plateform. An ultrafiltration membrane separates the container into two parts along the cross section of the container: the upper compartment, which is equipped with a stiffing apparatus and a gas inlet through which high purity nitrogen or argon enters; and the lower compartment, which is equipped with a liquid suction device for draining the allicin solution after removal of alliinase.

Embodiment 4

(1) Add 35.4 g alliinase with the enzyme activity of not less than 1000 IU/g and 1500 ml deoxygenated pure water to a container, stiffing thoroughly (M, 60 rpm) to completely dissolve the alliinase, adjusting the temperature of water bath to 35° C., and controlling the pH at 8.5, to obtain an alliinase solution, wherein the pure water was such water that was fresh boiled and naturally cooled, and then high purity nitrogen or argon was introduced at a speed of 10 L/h into the water from bottom to remove dissolved oxygen therein;

(2) Prepare an alliin solution, where the ratio of alliin to deoxygenated pure water was 35.4 g: 800 ml, dropwise add the alliin solution to the above container slowly, stiffing thoroughly at a stiffing speed of 60 rpm and continuously filling high purity nitrogen or argon so that the container was fully filled with the high purity nitrogen or argon, where the ratio of alliin:alliinase is 1 mg:1 IU, and the purity of alliin is higher than 90%;

(3) After completion of dropwise addition of the alliin solution, keep stiffing the mixed solution to conduct reaction for about 300 min in total, to obtain an enzymolysis reaction solution containing allicin and so on, and then immediately replace the warm bath water with ice water to lower down the temperature of water bath to 2° C., and finally, an ultrafiltration membrane of 5000 D was used to remove the alliinase and obtain an aqueous solution of allicin.

In the second step, the allicin formed in step 1 was diluted with precooled solvent (2° C.) in clean environment to obtain an allicin solution. The solvent was deoxygenated pure water, or deoxygenated pure water containing ethanol cryoprotectant, or deoxygenated pure water containing propylene glycol cryoprotectant.

The allicin solution above was encapsulated into different specification ampoules filled with nitrogen or argon as required and sealed. The therapeutics use of this allicin injection is for septicemia or tumors by intravenously guttae.

The concentration of allicin produced above is 2.5 mg/ml. The specification of allicin injection is 5 ml/Amp. The injection was packed with brown case and stored in 0~−20° C. The keeping time is 6-12 months.

A low-temperature continuous stirring ultrafiltration device for production of allicin injection comprises a wide neck container with a heat preservation case and a refrigeration platform. The wide neck container is placed on the plateform. An ultrafiltration membrane separates the container into two parts along the cross section of the container: the upper compartment, which is equipped with a stiffing apparatus and a gas inlet through which high purity nitrogen or argon enters; and the lower compartment, which is equipped with a liquid suction device for draining the allicin solution after removal of alliinase.

Finally, it should be understood that the above described embodiments are only preferred embodiments of the invention, but should not be used to limit the invention. Although the present invention has been illustrated with reference to the embodiments, the skilled in this field can modify the technical solutions described therein, or replace equivalent parts of technical features therein. All modifications, replacements or improvements, without departing from the principle and spirits of the invention, are within the protection scope of this invention.

What is claimed is:

1. A method for preparing an allicin solution comprising the following steps:
   (A) extracting allicin, which comprises the following steps:
   (1) adding alliinase and deoxygenated pure water to a container, in a water bath, filled with argon or high purity nitrogen in a water-to-alliinase ratio of 1000-2000 ml to 35.4 g, stirring thoroughly to completely dissolve the alliinase, adjusting the temperature of the water bath to 25-35° C., and controlling pH at 6.5-8.5 to obtain an alliinase solution;
   (2) preparing an alliin solution in a water-to-alliin ratio of 500-1000 ml to 35.4 g, adding the alliin solution dropwise into the container containing the alliinase solution, stirring thoroughly, and continuously filling the container with argon or high purity nitrogen so that the container is fully filled with the argon or high purity nitrogen, wherein a ratio of alliin to alliinase is 1 mg to 1-2 IU; and
   (3) after completion of the dropwise addition of the alliin solution, continuously stirring and reacting for 20 to 40 minutes in total to obtain an enzymolysis reaction solution containing allicin, immediately replacing warm water in the water bath with ice water to lower the temperature of the water bath to 0° C., and using an ultrafiltration membrane of 1000-5000 Da to remove alliinase to obtain an aqueous solution of allicin; and
   (B) diluting the aqueous solution of allicin with a solvent precooled to a temperature of 0-4° C. within a clean bio-safety cabinet to obtain an allicin solution.

2. The method according to claim 1, wherein the solvent is deoxygenated pure water, or deoxygenated pure water containing ethanol cryoprotectant, or deoxygenated pure water containing propylene glycol cryoprotectant.

3. The method according to claim 1, wherein the alliin has a purity higher than 90%.

4. The method according to claim 1, wherein the alliinase has enzyme activity higher than 1000 IU/g.

5. The method according to claim 1, wherein the stirring is conducted at a speed of 60-120 rpm.

6. The method according to claim 1, wherein the deoxygenated pure water is freshly boiled and naturally cooled pure water, and is filled with nitrogen or argon at bottom at 10 L/1 h to remove dissolved oxygen therein.

7. The method according to claim 1, further comprising a third step of obtaining an allicin injection by encapsulating the allicin solution into an ampule filled nitrogen or argon, wherein the allicin injection can be used to treat septicemia or tumors by intravenously guttae.

* * * * *